(12) United States Patent
Houston et al.

US008802095B2

(10) Patent No.: US 8,802,095 B2
(45) Date of Patent: Aug. 12, 2014

(54) INJECTABLE, NON-AQUEOUS SUSPENSION WITH HIGH CONCENTRATION OF THERAPEUTIC AGENT

(75) Inventors: Paul R. Houston, Hayward, CA (US); Guohua Chen, Sunnyvale, CA (US); Andrew Sheung-King Luk, Pleasanton, CA (US)

(73) Assignee: Durect Corporation, Cupertino, CA (US)

( * ) Notice: Subject to any disclaimer, the term of this patent is extended or adjusted under 35 U.S.C. 154(b) by 0 days.

(21) Appl. No.: 13/282,416

(22) Filed: Oct. 26, 2011

(65) Prior Publication Data

US 2012/0100149 A1   Apr. 26, 2012

Related U.S. Application Data

(63) Continuation of application No. 12/020,372, filed on Jan. 25, 2008, now abandoned.

(60) Provisional application No. 60/897,643, filed on Jan. 26, 2007.

(51) Int. Cl.
    *A61K 39/395*     (2006.01)
(52) U.S. Cl.
    USPC ............... 424/141.1; 424/130.1; 514/772; 514/44; 514/785; 514/1.1; 514/43
(58) Field of Classification Search
    None
    See application file for complete search history.

(56) References Cited

U.S. PATENT DOCUMENTS

| | | | |
|---|---|---|---|
| 6,482,850 B2 | 11/2002 | Ali et al. | |
| 7,250,165 B2 | 7/2007 | Heavner et al. | |
| 7,258,869 B1 * | 8/2007 | Berry et al. | 424/422 |
| 7,655,735 B2 * | 2/2010 | Seo et al. | 525/403 |
| 2002/0052518 A1 | 5/2002 | Ali et al. | |
| 2003/0108609 A1 | 6/2003 | Berry et al. | |
| 2004/0127551 A1 * | 7/2004 | Zhang et al. | 514/449 |
| 2004/0214758 A1 | 10/2004 | Meyers et al. | |
| 2005/0016926 A1 | 1/2005 | Burman et al. | |
| 2005/0026995 A1 | 2/2005 | Lee et al. | |
| 2005/0027019 A1 | 2/2005 | Zhang et al. | |
| 2005/0118206 A1 | 6/2005 | Luk et al. | |
| 2005/0239877 A1 | 10/2005 | Gomez et al. | |
| 2006/0142234 A1 * | 6/2006 | Chen et al. | 514/44 |

FOREIGN PATENT DOCUMENTS

| | | |
|---|---|---|
| WO | WO 95/01155 | 1/1995 |
| WO | WO 98/41188 | 9/1998 |
| WO | WO 99/24073 | 5/1999 |
| WO | WO 00/16744 | 3/2000 |
| WO | WO 01/15734 A2 | 3/2001 |
| WO | WO 03/045326 | 6/2003 |
| WO | WO 2005/009419 | 2/2005 |
| WO | WO 2005/017079 | 2/2005 |
| WO | WO 2005/041881 | 5/2005 |
| WO | WO 2005/048930 | 6/2005 |
| WO | WO 2005/118672 | 12/2005 |
| WO | WO 2006/050123 | 5/2006 |
| WO | WO 2006/071613 | 7/2006 |
| WO | WO 2006/071693 | 7/2006 |

OTHER PUBLICATIONS

Date et al., "Parenteral microemulsions: An overview," International Journal of Pharmaceutics 355 (2008) 19-30)( available on line Jan. 12, 2008).*
Woodcock et al., "Reversal of the Multidrug Resistance Phenotoype with Cremophor EL, A Common Vehicle for Water-insoluble Vitamins and Drugs," *Cancer Research* 50, 4199-4203, Jul. 15, 1990.

* cited by examiner

*Primary Examiner* — Suzanne Ziska

(57) ABSTRACT

An injectable, nonaqueous suspension including at least one therapeutic agent suspended in a single component vehicle. The single component vehicle is a single amphiphilic material, such as a polyethoxylated castor oil or derivative thereof, a polyoxyethylene alkyl ether, a polyoxyethylene sorbitan fatty acid ester, a polyoxyethylene stearate, a block copolymer of polyethylene oxide-polypropylene oxide-polyethylene oxide, a block copolymer of polypropylene oxide-polyethylene oxide-polypropylene oxide, a tetra-functional block copolymer of polyethylene oxide-polypropylene oxide, or a tetra-functional block copolymer of polypropylene oxide-polyethylene oxide. A dosage kit that includes the injectable, nonaqueous suspension and a method of administering the injectable, nonaqueous suspension are also disclosed.

20 Claims, 3 Drawing Sheets

INJECTABLE, NON-AQUEOUS SUSPENSION WITH HIGH CONCENTRATION OF THERAPEUTIC AGENT

This application is a continuation application of U.S. application Ser. No. 12/020,372, filed Jan. 25, 2008 now abandoned, all of which applications and patent are hereby incorporated herein by reference.

CROSS-REFERENCE TO RELATED APPLICATION

This application is a utility conversion and claims the benefit under 35 U.S.C. §119(e) of U.S. Provisional Patent Application No. 60/897,643 filed Jan. 26, 2007, entitled "INJECTABLE, NONAQUEOUS SUSPENSION WITH HIGH CONCENTRATION OF THERAPEUTIC AGENT."

TECHNICAL FIELD

The present invention relates to an injectable suspension that includes a therapeutic agent. More specifically, the present invention relates to an injectable, nonaqueous suspension that includes the therapeutic agent suspended in a single component vehicle.

BACKGROUND

Proteins and peptides have become powerful therapeutic agents in the treatment of various diseases, such as cancer, inflammatory, cardiovascular, respiratory, and infectious diseases. However, formulation and delivery of these molecules are challenging due to solubility and viscosity limitations. Except for highly potent molecules, formulations of these molecules need to contain relatively high concentrations of the protein to enable efficacious dose levels by subcutaneous ("SC") or intramuscular ("IM") routes of administration.

Commercialization strategies often involve lyophilized formulations that require reconstitution of the protein prior to being delivered by injection, which can add costs and time to the manufacturing process. Ready-to-use solution formulations of proteins and peptides, when feasible, can minimize this inconvenience. However, the requirement for a high concentration of the protein adds complexity to formulation design and promotes instability.

It has been estimated that greater than 20% of all biopharmaceuticals currently being evaluated in clinical trials are monoclonal antibodies ("mAbs"). In general, mAb therapies require the delivery of between approximately 100 mg and approximately 1 g of protein per dose. Because the high end of formulation concentrations for mAbs is typically in the range of 50 mg/ml, such treatments commonly require the administration of 2 to 20 ml. Typically, such volumes are administered only through intravenous ("IV") infusion performed in a clinical or hospital setting, which leads to poor patient compliance.

To achieve a high protein concentration, nonaqueous suspensions of proteins have been formulated. In these formulations, the protein is suspended in a vehicle that includes at least two of the following: a polymer, a surfactant, and a solvent. The formulation has a protein concentration of up to 500 mg/ml.

To expand therapeutic opportunities and increase patient compliance, a method of achieving a high concentration of mAbs is needed so that large protein doses are deliverable in a small volume appropriate for SC or IM injection. One possible approach is to prepare extremely high concentration preparations of soluble mAbs, on the order of 150 to 250 mg/ml. However, achieving such highly concentrated mAb solutions is problematic due to solubility limitations and/or relatively high viscosities, which often results in protein aggregation and poor overall stability.

Polyethoxylated castor oil (also known as polyoxyl castor oil, polyoxyl 35 castor oil, polyoxyethylated castor oil, macrogolglycerol ricinoleate, or macrogolglyceroli ricinoleas) has been used as a solvent for pharmaceutical compositions that include a hydrophobic drug, such as miconazole, echinomycin, teniposide, diazepam, althesin, or paclitaxel. The hydrophobic drug and the polyethoxylated castor oil form a solution. To further solubilize the hydrophobic drug, many of these pharmaceutical compositions also include an alcohol.

There remains a need to develop highly concentrated protein formulations to enable delivery of a variety of therapeutic proteins in a convenient way with a small volume.

SUMMARY OF THE INVENTION

The present invention relates to an injectable, nonaqueous suspension that includes at least one therapeutic agent suspended in a single component vehicle.

The present invention also relates to a dosage kit that includes a syringe and the injectable, nonaqueous suspension.

The present invention also relates to a method of administering a therapeutic agent that includes suspending the at least one therapeutic agent in the single component vehicle and injecting the injectable, nonaqueous suspension into a patient in need thereof.

BRIEF DESCRIPTION OF DRAWINGS

While the specification concludes with claims particularly pointing out and distinctly claiming that which is regarded as the present invention, the advantages of this invention may be more readily ascertained from the following description of the invention when read in conjunction with the accompanying drawings in which:

DETAILED DESCRIPTION OF THE INVENTION

Figure 1:
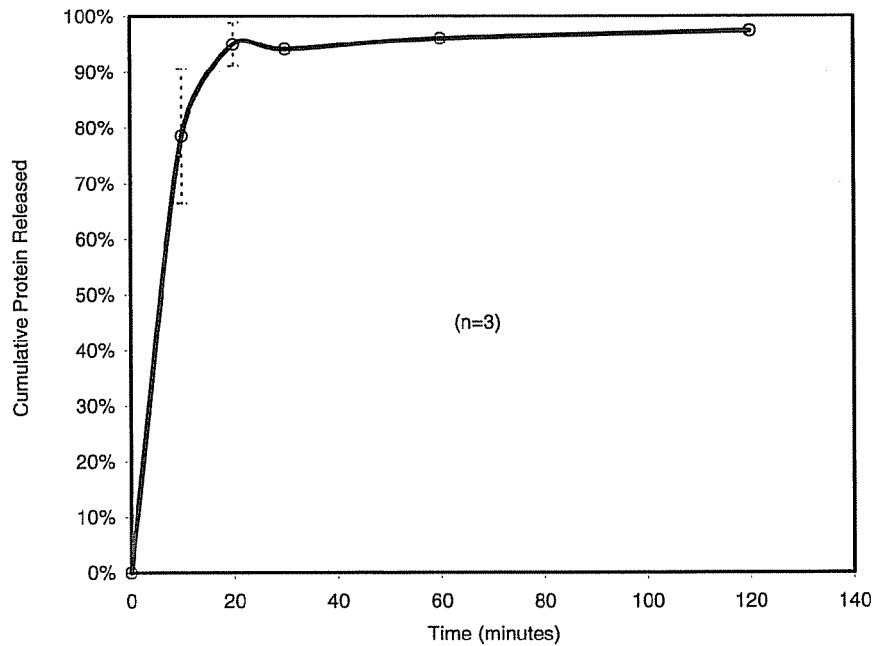
FIG. 1 is a graph showing in vitro release data for a bovine serum albumin ("BSA")/Cremophor® ELP formulation.

An injectable, nonaqueous suspension having at least one therapeutic agent and a single component vehicle is disclosed. The therapeutic agent is suspended in the single component vehicle. The injectable, nonaqueous suspension may be formulated to administer a high dose of the therapeutic agent in a small dose volume. For instance, the dose volume may be less than or equal to approximately 2 ml/injection. The injectable, nonaqueous suspension may provide immediate delivery of a low potency, therapeutic agent.

As used herein, the term "therapeutic agent" refers to a compound that provides a desired biological or pharmacological effect when administered to a human or animal. The therapeutic agent may be present as a solid in a dosage form of the injectable, nonaqueous suspension. The therapeutic agent may be minimally soluble or swellable in the single component vehicle, maintaining the therapeutic agent in a substantially solid form in the injectable, nonaqueous suspension. The solubility of the therapeutic agent in the injectable, nonaqueous suspension may be less than approximately 1% by weight ("wt %"), such as less than approximately 0.5 wt % or less than approximately 0.1 wt %. The therapeutic agent remains suspended in the injectable, nonaqueous suspension independent of the therapeutic agent's molecular structure or molecular weight. For the sake of example only, the therapeutic agent may be a small molecule, protein, antibody, mimetibody, mAb, antibody fragment (including a diabody, triabody, or tetrabody), peptide, enzyme, nucleotide, DNA fragment, RNA fragment, plasmid fragment, nucleotide fragment, or mixtures thereof. In one embodiment, the therapeutic agent is a mAb, such as CNTO 1275 or CNTO 148. CNTO 1275 is a human mAb to anti-IL-12/23p40, and is described in U.S. Pat. No. 6,902,734, the contents of which are hereby incorporated herein by this reference. CNTO 148 is an antibody against human TNF-a, and is described in U.S. patent application Ser. No. 09/920,137, filed Aug. 1, 2001, entitled "Anti-TNF Antibodies, Compositions, Methods and Uses," the contents of which are hereby incorporated herein by this reference. In another embodiment, the therapeutic agent is a protein or enzyme, such as BSA or lysozyme.

Alternatively, the therapeutic agent may be selected from the group consisting of baclofen, glial-cell line-derived neurotrophic factor, a neurotrophic factor, conatonkin G, Ziconotide, clonidine, axokine, an antisense oligonucleotide, adrenocorticotropic hormone, angiotensin I, angiotensin II, atrial natriuretic peptide, B-natriuretic peptide, bombesin, bradykinin, calcitonin, cerebellin, dynorphin N, alpha endorphin, beta endorphin, endothelin, enkephalin, epidermal growth factor, fertirelin, follicular gonadotropin releasing peptide, galanin, glucagon, glucagon-like peptide-1, gonadorelin, gonadotropin, goserelin, growth hormone releasing peptide, histrelin, human growth hormone, insulin, an alpha-, beta-, or omega-interferon, Nesiritide, leuprolide, luteinizing hormone-releasing hormone, motilin, nafarelin, neurotensin, oxytocin, relaxin, somatostatin, substance P, tumor necrosis factor, triptorelin, vasopressin, growth hormone, nerve growth factor, a blood clotting factor, and a ribozyme. In one embodiment, the at least one solvent is benzyl benzoate, the at least one polymer is polyvinylpyrrolidone, and the active agent is omega-interferon (omega-INF). The active agent may also be selected from small molecules such as, for example, ocaperidone, risperidone, and paliperidone.

The therapeutic agent may be formulated into particles having a particle size that ranges from approximately 0.1 μm to approximately 250 μm. The particles of the therapeutic agent may be produced by conventional processes including, but not limited to, mechanical milling and sieving or spray drying. To provide additional stability to the therapeutic agent, a stabilizer may, optionally, be present in the injectable, nonaqueous suspension. The stabilizer of the therapeutic agent may be a sugar, such as sucrose, trehalose, sorbitol, mannitol, a monosaccharide alcohol, or mixtures thereof. If the therapeutic agent is a protein, the therapeutic agent and, optionally, the stabilizer may be dissolved into a solution, which is lyophilized to produce particles of the therapeutic agent. These particles are ground and sieved to the desired particle size. Alternatively, the solution may be spray-dried or spray-freeze-dried to produce particles of the desired size. In addition to the stabilizer, the formulation of the therapeutic agent may, optionally, include at least one pH modifier.

The single component vehicle may be a single amphiphilic material having a liquid to semi-solid form. The amphiphilic material may be a solvent, surfactant, or excipient. As used herein, the term "single component vehicle" refers to a one-component vehicle. As such, the single component vehicle does not include additional solvents, surfactants, or excipients, which simplifies formulation of the injectable, nonaqueous suspension. As used herein, the term "amphiphilic" refers to a compound having a polar, water-soluble group attached to a nonpolar, water-insoluble group or chain. The term "liquid to semi-solid" refers to a material having intermediate properties, such as viscosity, between those of a solid and a liquid. The viscosity of the single component vehicle may be selected to provide the injectable, nonaqueous suspension with a low injection force when administered to a human or animal. The single component vehicle may have a melting point or a pour point of approximately room temperature (approximately 25° C.), so that the single component vehicle is a liquid or semi-solid at body temperature.

Examples of amphiphilic materials that may be used as the single component vehicle include, but are not limited to, a polyethoxylated castor oil or derivative thereof (collectively referred to herein as a "polyethoxylated castor oil"), a polyoxyethylene alkyl ether, a polyoxyethylene sorbitan fatty acid ester, a polyoxyethylene stearate, a block copolymer of polyethylene oxide ("PEO")-polypropylene oxide ("PPO")-PEO, a block copolymer of PPO-PEO-PPO, a tetra-functional block copolymer of PEO-PPO, such as (PEO-PPO)$_2$-(PPO-PEO)$_2$, or a tetra-functional block copolymer of PPO-PEO, such as (PPO-PEO)$_2$-(PEO-PPO)$_2$. In one embodiment, the single component vehicle is a polyethoxylated castor oil.

One example of a polyethoxylated castor oil is sold under the tradename Cremophor® and is commercially available from BASF Corp. (Mount Olive, N.J.). Cremophor® products of various purities and viscosities are produced by BASF Corp. and may be used in the present invention, such as Cremophor® A 25, Cremophor® A 6, Cremophor® EL, Cremophor® RH 40, Cremophor® ELP, or mixtures thereof. Cremophor® ELP and Cremophor® EL are nonionic solubilizers and emulsifiers produced by reacting castor oil with ethylene oxide in a molar ratio of 1 to 35. Cremophor® RH 40 is a nonionic solubilizer and emulsifier produced by reacting castor oil with ethylene oxide in a molar ratio of 1 to 45. While the composition of Cremophor® products is proprietary, it is believed that the reaction product of castor oil and ethylene oxide includes a complex mixture of unmodified castor oil and a variety of polyethylene glycols, polyethoxylated glycerol, polyethoxylated fatty acids, and mono-, di- and triesters of glycerol that are polyethoxylated to differing degrees. In one embodiment, the single component vehicle is Cremophor® ELP, which has a viscosity of between approximately 600 mPa·sec and approximately 750 mPa·sec at 25° C. In another embodiment, the single component vehicle is Cremophor® EL, which has a viscosity of between approximately 700 mPa·sec and approximately 800 mPa·sec at 25° C. In another embodiment, the single component vehicle is Cremophor® RH 40. A 30% aqueous solution of Cremophor® RH 40 has a Hoeppler viscosity at 25° C. of between approximately 20 mPa·sec and approximately 40 mPa·sec.

Examples of polyoxyethylene alkyl ethers that may be used as the single component vehicle include, but are not limited to, Brij® 35, Brij® 52, Brij® 56, Brij® 93, Brij® 97, Brij® 99, Ethylan® 256, Ethylan® 257, Ethylan® 2512, Renex® 30, Renex® 31, Texofor AP, Texofor A6, Texofor A10, or mixtures thereof. Examples of polyoxyethylene sorbitan fatty acid esters include, but are not limited to, polysorbate 61, polysorbate 65, polysorbate 80, or mixtures thereof. Examples of polyoxyethylene stearates include, but are not limited to, polyoxyl 6 stearate, polyoxyl 8 stearate, polyoxyl 12 stearate, polyoxyl 20 stearate, polyoxyl 40 stearate, polyoxyl 12 distearate, or mixtures thereof. Examples of PEO-PPO-PEO include, but are not limited to, Pluronic® L44, Pluronic® L64, Pluronic® L122, Pluronic® P65, Pluronic® P75, Pluronic® P84, Pluronic® P85, Pluronic® P103, Pluronic® P104, Pluronic® P105, Pluronic® P123, or mixtures thereof. Examples of PPO-PEO-PPO include, but are not limited to, Pluronic® R 10R5, Pluronic® 17R4, Pluronic® 22R4, Pluronic® 25R4, Pluronic® 25R5, Pluronic® 31R4, or mixtures thereof. Examples of (PEO-PPO)$_2$-(PPO-PEO)$_2$ include, but are not limited to, Tetronic® 704, Tetronic® 904, Tetronic® 1104, or mixtures thereof. Examples of (PPO-PEO)$_2$-(PEO-PPO)$_2$ include, but are not limited to, Tetronic® R 50R8, Tetronic® 90R4, Tetronic® 150R4, or mixtures thereof.

A high concentration of the therapeutic agent may be suspended in the single component vehicle, enabling delivery of the therapeutic agent in a relatively small volume. For instance, the therapeutic agent may be present in the injectable, nonaqueous suspension at a concentration of up to approximately 500 mg/ml. For instance, the therapeutic agent may be present in the injectable, nonaqueous suspension at a concentration that ranges from greater than or equal to approximately 50 mg/ml to approximately 500 mg/ml. Such high concentrations of therapeutic agent would not be achievable in an aqueous formulation. Since the therapeutic agent is present at such a high concentration, the injectable, nonaqueous suspension may be used to deliver a therapeutic agent that has a low potency.

In a particular embodiment, the therapeutic agent may account for from approximately 5% by weight ("wt %") of a total weight of the injectable, nonaqueous suspension to approximately 50 wt % of the total weight of the injectable, nonaqueous suspension. For instance, the therapeutic agent loading may range from approximately 10 wt % of the total weight of the injectable, nonaqueous suspension to approximately 50 wt % of the total weight of the injectable, nonaqueous suspension.

The injectable, nonaqueous suspension may be produced by mixing the particles of the therapeutic agent into the single component vehicle by techniques known in the art. Since the therapeutic agent and the single component vehicle are combined using conventional techniques, production of the injectable, nonaqueous suspension is not described in detail herein. The particles of the therapeutic agent may be substantially homogeneously dispersed in the single component vehicle, producing a substantially homogeneous injectable, nonaqueous suspension.

The injectable, nonaqueous suspension may, optionally, include a small amount of at least one antioxidant. The antioxidant may be d-alpha tocopherol acetate, dl-alpha tocopherol, ascorbyl palmitate, butylated hydroxyanidole, ascorbic acid, butylated hydroxyanisole, butylatedhydroxyquinone, butylhydroxyanisol, hydroxycomarin, butylated hydroxytoluene, cephalm, ethyl gallate, propyl gallate, octyl gallate, lauryl gallate, propylhydroxybenzoate, trihydroxybutylrophenone, dimethylphenol, diterlbulylphenol, vitamin E, lecithin, ethanolamine, or mixtures thereof. If an antioxidant is present in the injectable, nonaqueous suspension, the antioxidant may be premixed with the therapeutic agent before mixing with the single component vehicle. Alternatively, the antioxidant may be premixed with the single component vehicle before mixing with the therapeutic agent or may be loaded separately into the single component vehicle.

The injectable, nonaqueous suspension may be preloaded in a syringe and, therefore, is injection ready without mixing or reconstitution. The injectable, nonaqueous suspension may be loaded into the syringe by conventional techniques, which are well known in the art and, thus, are not described in detail herein. Since the therapeutic agent remains in a substantially solid form, the injectable, nonaqueous suspension can have a long shelf life stability. The injectable, nonaqueous suspension may be fluidly injectable at 25° C. The injectable, nonaqueous suspension in the preloaded syringe may be injected by hand. Alternatively, the preloaded syringe may be used with an autoinjector, where injection of the injectable, nonaqueous suspension is powered by the mechanical force of the autoinjector.

A dosage kit that includes the injectable, nonaqueous suspension and at least one syringe is also disclosed. In one embodiment, the syringe is an auto-injector syringe. In another embodiment, the syringe is divided such that the therapeutic agent and the single component vehicle remain separate until being mixed before injection. In another embodiment, two syringes are provided in the dosage kit. One syringe may contain the therapeutic agent while the other syringe may contain the single component vehicle. The contents of the first and second syringes may be combined before injection. The injectable, nonaqueous suspension may be administered to a patient or animal by any route, such as by SC or IM administration. Since the single component vehicle has a low viscosity, the injectable, nonaqueous suspension may have a low injection force. For instance, the injection force may be less than or equal to approximately 50 lbf, such as less than or equal to approximately 30 lbf or less than or equal to approximately 20 lbf.

The following examples serve to explain embodiments of the present invention in more detail. These examples are not to be construed as being exhaustive or exclusive as to the scope of this invention.

EXAMPLES

In vitro release experiments were conducted to test suspension formulations to demonstrate release of the therapeutic agent into a buffer solution. The in vitro release characteristics are related to in vivo release characteristics. Injection force experiments were performed to test the injectability of the suspension formulations because injectability is an important performance characteristic. Stability is also an important performance characteristic for suspension formulations. Therefore, sampling was conducted at extended time intervals to demonstrate stability of the therapeutic agent. Biocompatibility tests were also conducted to demonstrate tolerance to the suspension injection in a rat model.

Example 1

Preparation of Lysozyme Particles

A lysozyme solution was prepared by dissolving lysozyme (available from Sigma-Aldrich Corp. (St. Louis, Mo.)) in 6.5 mM sodium phosphate buffer, pH 6.0, at a protein concentration of 65 mg/mL. Sucrose and Tween 80 (or polysorbate 80) were optionally added to the lysozyme solution with the concentration of sucrose and Tween 80 in the final solution of 0%-5.5% and 0%-0.0065% weight/volume, respectively. The lysozyme solution was lyophilized according to the conditions shown in Table 1.

TABLE 1

Lyophilization Conditions for the Preparation of Lysozyme Particles.

| Process Step | Shelf Temperature (° C.) | Chamber Pressure (mBar) | Hold Time (hours) |
|---|---|---|---|
| Loading | +5 | N/A | 2 |
| Freezing | −50 (rate 0.5° C.) | N/A | 2 |
| Freezing | −50 | N/A | 2.5 |
| Vacuum on | −50 | 120 mT | 0.5 |
| Vacuum hold | −50 | 120 mT | 0.5 |
| 1° Drying | −10 (rate 1° C./minute) | 120 mT | 0.75 |
| 1° Drying | −10 | 120 mT | 24 |
| 2° Drying | 0 (rate 0.1° C./minute) | 80 mT | 1.7 |
| 2° Drying | 0 | 80 mT | 2 |
| 2° Drying | +35 (rate 0.25° C./minute) | 80 mT | 2.3 |
| 2° Drying | +35 | 80 mT | 10 |
| 2° Drying | +20 (rate 1° C./minute) | 80 mT | 0.25 |
| 2° Drying | +20 | 80 mT | 2 |
| Minimum Total time = | | | 50.5 hours |

Lysozyme particles having the desired particle size were prepared by grinding the lyophilized lysozyme in a Waring blender and passing the particles through a series of sieves having determined mesh sizes. Lysozyme particles having a particle size of less than approximately 38 µm, between from approximately 38 µm to approximately 63 µm, less than approximately 125 µm, and less than approximately 250 µm were produced by this process. Alternatively, lysozyme particles were prepared by diluting the lyophilized lysozyme described above to a concentration of approximately 20 mg/ml with deionized water and spray drying the solution, resulting in lysozyme particles having a particle size that ranged from approximately 1 µm to approximately 10 µm.

Example 2

Preparation of BSA Particles

BSA particles were produced according to the methods described in Example 1, except hat BSA was used in place of lysozyme.

Example 3

Preparation of CNTO 1275 Particles

Particles of a mAb were produced by dissolving CNTO 1275 in 6.5 mM sodium phosphate buffer with sucrose (concentration of 5.5% w/v), pH 6.0, with a protein concentration of 65 mg/mL. To the solution of CNTO 1275 was added 0.0065% w/v of Tween 80 (or polysorbate 80). The solution was lyophilized according to the conditions shown in Table 2.

TABLE 2

Lyophilization Conditions for Preparation of CNTO 1275 Particles.

| Process Step | Shelf Temperature (° C.) | Chamber Pressure (mBar) | Hold Time (hours) |
|---|---|---|---|
| Loading | +5 | N/A | 2 |
| Freezing | −50 (rate 0.5° C.) | N/A | 2 |
| Freezing | −50 | N/A | 2.5 |
| Vacuum on | −50 | 120 mT | 0.5 |
| Vacuum hold | −50 | 120 mT | 0.5 |
| 1° Drying | −10 (rate 1° C./minute) | 120 mT | 0.75 |
| 1° Drying | −10 | 120 mT | 24 |
| 2° Drying | 0 (rate 0.1° C./minute) | 80 mT | 1.7 |
| 2° Drying | 0 | 80 mT | 2 |
| 2° Drying | +35 (rate 0.25° C./minute) | 80 mT | 2.3 |
| 2° Drying | +35 | 80 mT | 10 |
| 2° Drying | +20 (rate 1° C./minute) | 80 mT | 0.25 |
| 2° Drying | +20 | 80 mT | 2 |
| Minimum Total time = | | | 50.5 hours |

CNTO 1275 particles having a particle size of less than approximately 125 µm were prepared by grinding the lyophilized formulation in a Waring blender and sieving through a 120 mesh sieve.

Example 4

Preparation of Nonaqueous Suspensions

Nonaqueous suspensions of lysozyme, BSA, or CNTO 1275 particles were prepared. The particles (lysozyme, BSA, or CNTO 1275), which were prepared as described in Examples 1-3, were mixed with Cremophor® ELP or Cremophor® RH 40 using an overhead mixer. The mixing was performed at room temperature inside a dry box. The particles and Cremophor® ELP or Cremophor® RH 40 were weighed and transferred into a 25 cc glass syringe. The particle loading was from approximately 20 wt % to approximately 50 wt %, resulting in a protein concentration in a final formulation of from approximately 120 mg/ml to approximately 500 mg/mL. An electric stirrer with a stainless steel spatula blade was used to blend the particles into the Cremophor® ELP or Cremophor® RH 40 at from approximately 50 rpm to approximately 300 rpm for approximately 5 minutes. The suspensions were filled into glass injection syringes, yielding an injection ready dosage form. The suspensions were stored at a refrigerated temperature (approximately 4° C. to approximately 5° C.) prior to injection.

Example 5

In Vitro Release Testing of a BSA/Cremophor® ELP Formulation

Spray-dried BSA particles were mixed with Cremophor® ELP at a ratio of 37 wt % BSA particles and 63 wt % Cremophor® ELP. Three 50-60 mg samples of the BSA/Cremophor® ELP suspension were placed in vials along with PBS buffer solution. The vials were placed on a shaker in a 37° C. oven. Samples of the supernatant were removed from the vials at various time points to determine the BSA content, and fresh PBS solution of the same (removed) volume was added back to the vials. The supernatant was analyzed using UV Spectroscopy to determine the BSA content. A graph of the cumulative protein released versus time is shown in FIG. 1. Approximately 95% of the BSA was released from the suspension within approximately 20 minutes of the test initiation, indicating the protein in the suspension of Cremophor® ELP was released into the medium instantaneously. As such, the Cremophor® ELP does not trap the therapeutic agent to cause a depot effect.

Example 6

Injection Force Testing of BSA/Cremophor® ELP Formulation

Injectability of a BSA/Cremophor® ELP suspension was determined by measuring the force required to push the suspension through a fine gauge needle. Cremophor® ELP and BSA particles having a particle size of less than or equal to approximately 125 μm were blended in a ratio of 60:40 by weight, respectively. The suspension was loaded into three Hamilton 500 μl Gastight® syringes. The syringes were filled with approximately 0.4 cc of the suspension and aluminum hub hypodermic needles (21-gauge, 1 inch (2.54 cm) in size) were placed on each syringe. The syringes were packaged, three syringes to each polyethane bag, and stored in the refrigerator at approximately 5° C. At 1-, 5-, 28-, and 36-week time periods, samples were removed from the refrigerator for injection force testing. The syringes were equilibrated to room temperature (approximately 25° C.) for at least two hours before testing. The injection rate was set at approximately 1 ml/minute, which is equivalent to a crosshead speed of 4.7 inch (11.938 cm)/minute. The injection testing was conducted at room temperature and the peak (maximum) force value was recorded. Injection force testing was carried out on a Mini-55 Instron tensile testing instrument.

Figure 2:
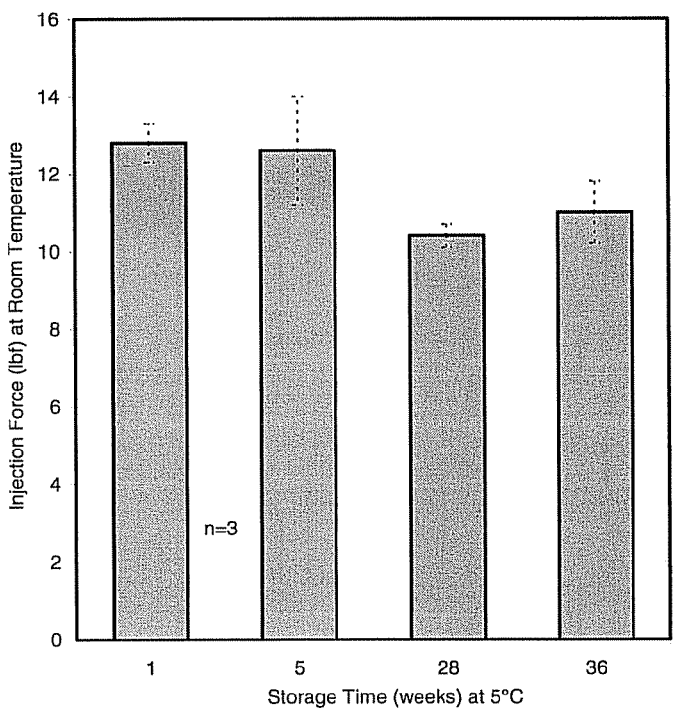
FIG. 2 is a graph showing injection force data for a BSA/Cremophor® ELP formulation.

The injection force at room temperature versus storage time at 5° C. for the BSA/Cremophor® ELP suspension is shown in FIG. 2. No increase in the force required to dispense the BSA/Cremophor® ELP suspension was observed as a function of storage time, which demonstrates that the BSA/Cremophor® ELP suspension is physically stable in the described time frames. No settling of the BSA particles in the Cremophor® ELP was observed.

Example 7

Injection Force Testing of BSA/Cremophor® RH 40 Suspension

Injectability of a BSA/Cremophor® RH 40 suspension was determined by measuring the force required to push the suspension through a fine gauge needle. Cremophor® RH 40 and BSA particles having a particle size of less than or equal to approximately 125 μm were blended in a ratio of 60:40 by weight, respectively. The suspension was loaded into three Hamilton 500 μl Gastight® syringes. The syringes were filled with approximately 0.4 cc of the suspension and aluminum hub hypodermic needles (21-gauge, 1 inch (2.54 cm) in size) were placed on each syringe. The syringes were packaged, three syringes to each polyethane bag, and stored in the refrigerator at approximately 5° C. Samples were removed from the refrigerator at 5 days and at 180 days for the injection force testing. The syringes were equilibrated to room temperature for at least two hours before the testing. The injection rate was set at approximately 1 ml/minute, which is equivalent to a crosshead speed of 4.7 inch (11.938 cm)/minute. The injection testing was conducted at room temperature and the peak (maximum) force value was recorded. Injection force testing was carried out on a Mini-55 Instron tensile testing instrument.

Figure 3:
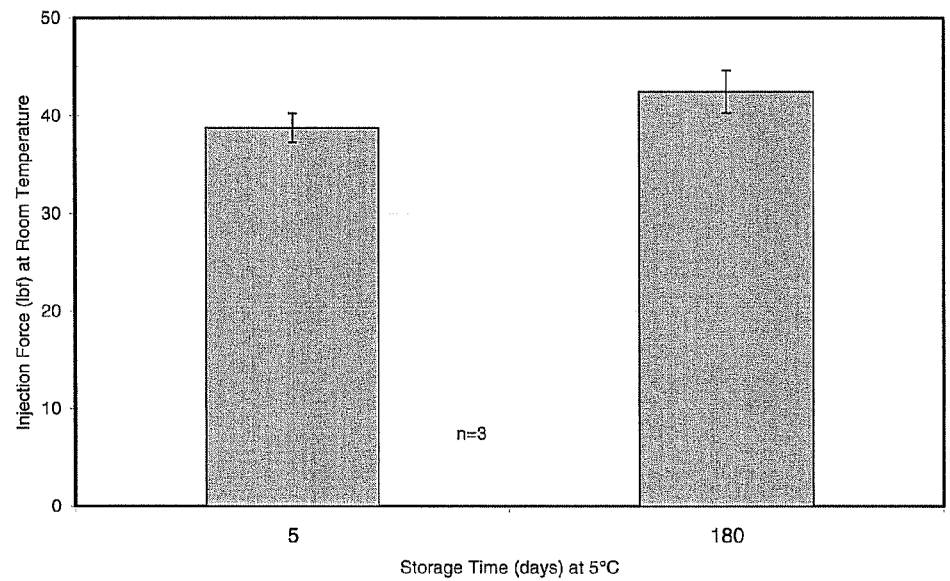
FIG. 3 is a graph showing injection force data for a BSA/Cremophor® RH 40 formulation.

The injection force at room temperature versus storage time at 5° C. for the BSA/Cremophor® RH 40 suspension is shown in FIG. 3. No increase in the force required to dispense the BSA/Cremophor® RH 40 suspension was observed as a function of storage time, which demonstrates that the BSA/Cremophor® RH 40 suspension is physically stable in these time frames. No settling of the BSA particles in the Cremophor® RH 40 was observed.

Example 8

Stability of CNTO 1275/Cremophor® ELP Formulation

Cremophor® ELP was cleaned with aluminum oxide powder to reduce the peroxide level and was passed through sterile, 0.2 μm PTFE filters. Two 10 mg portions of CNTO 1275 were weighed into vials for each stability time point. Into each vial, 0.1 ml of cleaned Cremophor® ELP was added. The CNTO 1275/Cremophor® ELP samples were then mechanically stirred and caps were placed on each vial. The vials were removed from the dry box and placed in a refrigerator at 5° C. CNTO 1275 particles, without Cremophor® ELP, were stored with the suspension samples as a control. A control formulation that included 25% polyvinylpyrollidone ("PVP") and 75% ultrapure polyethylene glycol 400 ("PEG 400") was also stored with the suspension samples. At 0-, 1-, 4-, 8-, and 12-week intervals, samples were removed from the refrigerator and tested for monomer content by size exclusion chromatograph ("SEC.")

Figure 4:
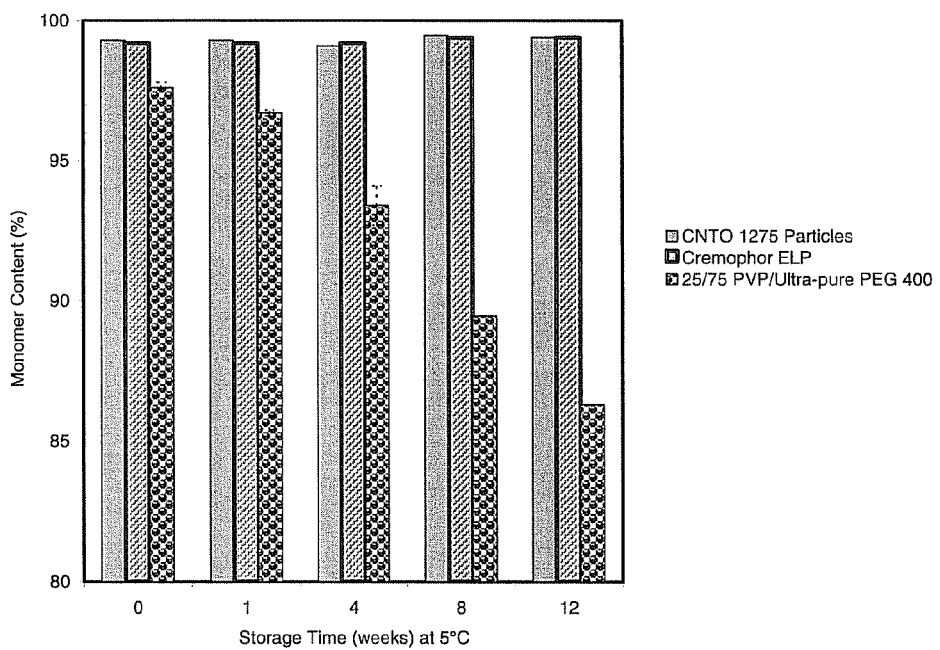
FIG. 4 is a graph showing stability data for a monoclonal antibody ("mAb") CNTO 1275/Cremophor® ELP formulation.

A graph of monomer content versus storage time at 5° C. is shown in FIG. 4. The results show that CNTO 1275 in Cremophor® ELP (labeled "Cremophor ELP" in FIG. 4) had the same monomer content as CNTO 1275 particles without Cremophor® ELP (labeled "CNTO 1275 Particles" in FIG. 4) at each time point, which demonstrates that the Cremophor® ELP vehicle did not degrade the CNTO 1275 monoclonal antibody within 12 weeks of storage time at 5° C. In comparison, significant protein aggregation was observed with the formulation that included the CNTO 1275 particles, 25% PVP, and 75% PEG 400, which is shown by the reduced monomer content.

Example 9

Biocompatibility of Cremophor® ELP

Figure 5:
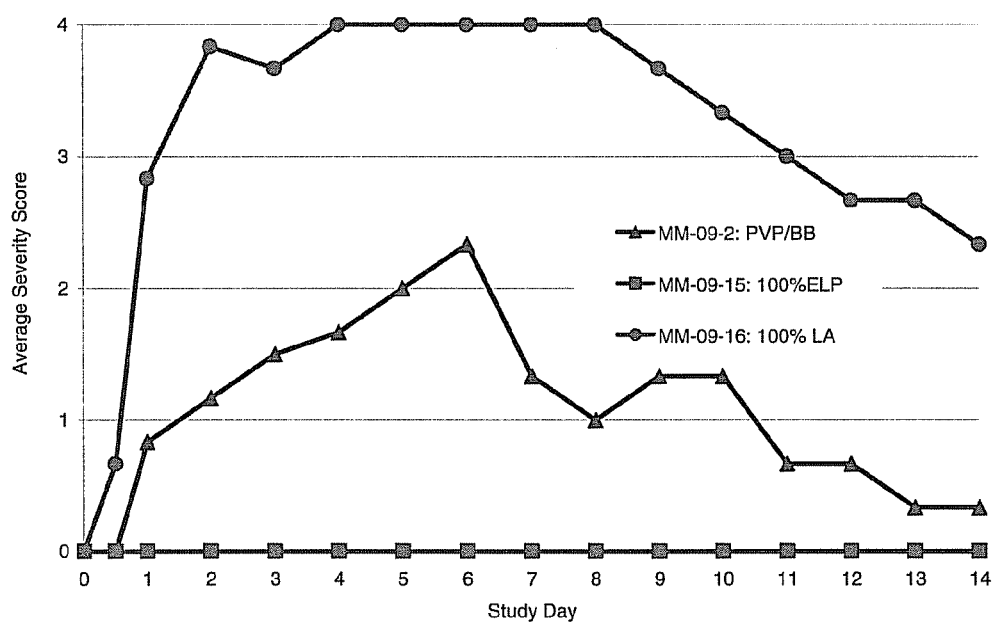
FIG. 5 is a graph showing biocompatibility data for Cremophor® ELP.

Cremophor® ELP was cleaned with aluminum oxide powder to reduce the peroxide level and was passed through sterile, 0.2 μm PTFE filters. The cleaned Cremophor® ELP was transferred into 0.25 ml autoclaved glass syringes. Each syringe was filled with between 0.155 ml and 0.160 ml of Cremophor® ELP. The syringes were fitted with 23 gauge, 1-inch (2.54 cm) aluminum hub hypodermic needles to deliver a 0.100 ml subcutaneous injection into rats. The Cremophor® ELP was administered at six injection sites. The injection sites were qualitatively assessed for swelling and irritation each day for two weeks. Injection sites were scored as "0" for no swelling and irritation, "1" for minimal swelling and irritation, "2" for mild swelling and irritation, "3" for moderate swelling and irritation, and "4" for severe swelling and irritation. Suspension vehicles of PVP/benzyl benzoate ("BB") (30%/70%) and lauryl alcohol ("LA") were used as controls. A graph of the average severity score versus study day is shown in FIG. 5. The Cremophor® ELP injections showed no swelling at the rat injection sites. The Cremophor® ELP received the best test score of "0" each of the 14 days that the injection sites were observed. In comparison, minimal to moderate swelling at the injection sites were observed with the PVP/BB and LA controls.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. An injectable, nonaqueous suspension comprising at least one therapeutic agent comprising solid particles suspended in a vehicle consisting of a single component vehicle consisting of an amphiphilic material,
   wherein the single component vehicle consists of a polyoxyethylene alkyl ether, a polyoxyethylene stearate, a block copolymer of polypropylene oxide-polyethylene oxide-polypropylene oxide, a tetra-functional block copolymer of polyethylene oxide-polypropylene oxide, or a tetra-functional block copolymer of polypropylene oxide-polyethylene oxide.

2. The injectable, nonaqueous suspension of claim 1, wherein the at least one therapeutic agent comprises a small molecule, protein, antibody, mimetibody, monoclonal antibody, antibody fragment, peptide, nucleotide, DNA fragment, RNA fragment, plasmid fragment, nucleotide fragment, or mixture thereof.

3. The injectable, nonaqueous suspension of claim 1, wherein the at least one therapeutic agent is present at a concentration that ranges from greater than or equal to approximately 50 mg/ml to approximately 500 mg/ml.

4. The injectable, nonaqueous suspension of claim 1, wherein the at least one therapeutic agent comprises from approximately 5% by weight of a total weight of the injectable, nonaqueous suspension to approximately 50% by weight of the total weight of the injectable, nonaqueous suspension.

5. The injectable, nonaqueous suspension of claim 1, further comprising at least one antioxidant.

6. The injectable, nonaqueous suspension of claim 1, wherein the suspension has an injection force that is less than or equal to about 50 lbf.

7. The injectable, nonaqueous suspension of claim 1, wherein the injectable, nonaqueous suspension consists essentially of the at least one therapeutic agent and the single component vehicle.

8. The injectable, nonaqueous suspension of claim 1, wherein the injectable, nonaqueous suspension consists of the at least one therapeutic agent and the single component vehicle.

9. A dosage kit comprising a syringe and an injectable, nonaqueous suspension, the injectable, nonaqueous suspension comprising at least one therapeutic agent comprising solid particles suspended in a vehicle consisting of a single component vehicle consisting of an amphiphilic material,
   wherein the single component vehicle consists of a polyoxyethylene alkyl ether, a polyoxyethylene sorbitan fatty acid ester, a polyoxyethylene stearate, a block copolymer of polypropylene oxide-polyethylene oxide-polypropylene oxide, a tetra-functional block copolymer of polyethylene oxide-polypropylene oxide, or a tetra-functional block copolymer of polypropylene oxide-polyethylene oxide.

10. The dosage kit of claim 9, wherein the at least one therapeutic agent comprises a small molecule, protein, antibody, mimetibody, monoclonal antibody, antibody fragment, peptide, nucleotide, DNA fragment, RNA fragment, plasmid fragment, nucleotide fragment, or mixture thereof.

11. The dosage kit of claim 9, wherein the injectable, nonaqueous suspension consists essentially of the at least one therapeutic agent and the single component vehicle.

12. The dosage kit of claim 9, wherein the injectable, nonaqueous suspension consists of the at least one therapeutic agent and the single component vehicle.

13. A method of administering a therapeutic agent, comprising:
   suspending at least one therapeutic agent comprising solid particles in a vehicle consisting of a single component amphiphilic vehicle to form an injectable, nonaqueous suspension; and
   injecting the injectable, nonaqueous suspension into a patient in need thereof,
   wherein the single component amphiphilic vehicle is selected from a polyoxyethylene alkyl ether, a polyoxyethylene sorbitan fatty acid ester, a polyoxyethylene stearate, a block copolymer of polypropylene oxide-polyethylene oxide-polypropylene oxide, a tetra-functional block copolymer of polyethylene oxide-polypropylene oxide, and a tetra-functional block copolymer of polypropylene oxide-polyethylene oxide.

14. The method of claim 13, wherein the at least one therapeutic agent comprises a small molecule, protein, antibody, mimetibody, monoclonal antibody, antibody fragment, peptide, nucleotide, DNA fragment, RNA fragment, plasmid fragment, nucleotide fragment, or mixture thereof in the single component vehicle.

15. The method of claim 13, wherein the at least one therapeutic agent is present at a concentration that ranges from greater than or equal to approximately 50 mg/ml to approximately 500 mg/ml.

16. The method of claim 13, wherein the at least one therapeutic agent comprises from approximately 5% by weight of a total weight of the injectable, nonaqueous suspension to approximately 50% by weight of the total weight of the injectable, nonaqueous suspension.

17. The method of claim 13, wherein the injectable, nonaqueous suspension consists essentially of the at least one therapeutic agent and the single component amphiphilic vehicle.

18. The injectable, nonaqueous suspension of claim 1, wherein the solid particles have a particle size ranging from approximately 0.1 µm to approximately 250 µm.

19. The dosage kit of claim 9, wherein the solid particles have a particle size ranging from approximately 0.1 µm to approximately 250 µm.

20. The method of claim 13, wherein the solid particles have a particle size ranging from approximately 0.1 µm to approximately 250 µm.

* * * * *